United States Patent [19]

Haski

[11] Patent Number: 4,949,729
[45] Date of Patent: Aug. 21, 1990

[54] GRIP RATE MEASUREMENT

[75] Inventor: Andre L. Haski, Dover Heights, Australia

[73] Assignee: Benjamin Dextronics Pty. Limited, Dover Heights, Australia

[21] Appl. No.: 23,171

[22] Filed: Mar. 9, 1987

[30] Foreign Application Priority Data

Mar. 12, 1986 [AU] Australia .............................. PH4980

[51] Int. Cl.$^5$ ............................................ A61B 5/103
[52] U.S. Cl. .................................... 128/774; 128/782; 73/379
[58] Field of Search ....................... 128/772, 774, 782; 73/379-381

[56] References Cited

U.S. PATENT DOCUMENTS 4,231,255 11/1980 Haski et al. ........................ 128/774

OTHER PUBLICATIONS

Blesser, A Systems Approach to Biomedicine, 1981, p. 221.

Primary Examiner—Max Hindenburg
Assistant Examiner—J. P. Lacyk
Attorney, Agent, or Firm—Todd S. Parkhurst

[57] ABSTRACT

An apparatus for the objective and quantitative measure of hand function comprising an inflatable bladder 1 in fluid communication with a pressure transducer 3 the output of which is connected to a programmable integrated circuit 9 which accords the change in pressure of the fluid within the bladder and calculates the rate of change of the logarithm of the pressure with respect to time between predetermined lower and upper pressure levels during which the rate of change is substantially linear, and display means 11, 12 and 13 for diplaying said rate of change of logarithmic pressure with respect to time as well as the maximum pressure achieved, the elapsed time at which the predetermined lower and upper pressures and a third predetermined intermediate pressure are attained and the correlation coefficient of said linear portion. The rate of change of the logarithmic pressure with respect to time or grip rate has been found to be a measure of the functionality of the hand and to be independent of age, sex and strength and to be substantially identical for both the left hand and the right hand.

8 Claims, 1 Drawing Sheet

GRIP RATE MEASUREMENT

FIELD OF THE INVENTION

The present invention relates to the detection and measurement of disorders of joint function by the measurement of the rate of movement of a joint against a resistance. Whilst the preferred embodiment of the invention to be described below particularly applies to the assessment of hand function and grip, the present invention is also applicable to different body joints.

BACKGROUND OF THE INVENTION

It is known that patients suffering from Repetitive Strain Injury, Rheumatoid Arthritis, Multiple Sclerosis, Strokes, head injuries with hemipareses and neuro-muscular diseases, and like diseases suffer from an alteration in the ability to physically grip an object.

The limitations of human static hand function measurement, lie in their inability to measure the hand as an integrated dynamic total system. Various instruments had been evolved to measure particular aspects of hand function such as grip-strength to the ninety-fifth percentile or stiffness within a joint such instruments permitted the demonstration of loss of grip-strength or stiffness within a joint, but did not go far enough towards demonstrating why there had been a loss of function.

The weakness of earlier instruments lay also in their inability to provide a clinical measure of hand function in the total sense. While they could be said to measure particular aspects of hand function and were therefore of use in monitoring rheumatic diseases, they were not capable of picking up the inter-relatedness of muscle, tendon and joint function and dysfunction. Such limitations reduced their usefulness as a monitor of integrated hand function.

It has long been known to measure the pressure in a compressible object as a function of time by means of chart recorders and like instruments. It is also known from Australian Patent No. 516026 (to which U.S. Pat. No. 231255 Haski et al corresponds) to provide an instrument which measures the elapsed time between the achievement of predetermined pressure values during the compression of a bladder. The apparatus disclosed in the above mentioned patent provided an instrument which enabled a medical practitioner to determine, by skilled interpretation of the numerical pressure/time data provided, the progress of treatment for a muscular disorder by ascertaining at an early date whether the patient was responding to the treatment.

Notwithstanding the improvement in clinical assessment provided by the above instrument, there exists a need to measure and assess the actual loss of function in a joint or joints in an objective and quantitative manner. For example, in some forms of medical conditions such as Repetitive Strain Injury, the symptoms experienced by the patient may in some instances be perceived mentally rather than actually experienced and the ability to objectively and quantitatively measure any loss of function would therefore greatly enhance the assessment of such persons. Similarly, a method of objectively and quantitatively measuring joint function would also assist in accident cases where one of two hands, for example, has been damaged and financial damages are to be assessed.

BRIEF SUMMARY OF THE INVENTION

As a result of extensive research flowing from the inventor's previous invention described in the above numbered patents, it has been determined that by measuring a new parameter, which the inventor has called "grip rate", or the rate at which a hand, or other joint, grips a compressible object, the functionality of the hand or joint under consideration can be assessed in an essentially objective and quantitative manner. This new parameter will enable a medical practitioner to determine whether the system experienced by a patient are muscular, neurological, joint stiffness related or psychosomatically induced, and the appropriate treatment can then be devised.

It is therefore an object of the present invention to provide an apparatus and method for objectively and quantitatively measuring the movement of a joint against a resistance, and measuring the grip rate, or the rate at which a patient grips, in order to provide an improved facility for assessment or treatment.

According to one aspect of the present invention, there is provided an apparatus for measuring the rate at which the movement of a joint compresses a compressible object, said apparatus comprising a fluid filled compressible object, such as an inflatable bladder, a pressure transducer in fluid communication with said object, said pressure transducer having output means connected to circuit means which includes means for determining the rate of change with time of the logarithm of the pressure of the fluid in said object between predetermined lower and upper pressure levels between which said rate of change is substantially herein, and displaying or recording means connected to said circuit means to display or record said rate of logarithmic pressure change with time.

In a preferred form of the invention, the circuit means also records the elapsed time at which the predetermined lower and upper pressures, and a third predetermined intermediate pressure, are attained during a substantially linear portion of the log pressure v time function, and calculates the correlation coefficient of this linear portion to thereby give a measure of the "straightness" or "linearity" of the linear portion which provides the operator with a means of assessing the efficiency of the grip-action of the patient. The circuit means may be arranged to allow the operator to select any one of a number of predetermined pressures, and in the case of the assessment of a hand function, the pressures for a relatively normal hand may be 60, 120 and 180 mm Hg whereas for a hand known to be affected say by rheumatoid arthritis, the pressure levels 45, 60, 120 mm Hg would be selected.

According to another aspect of the present invention, there is provided a method of assessing the functionality of a joint or joints, comprising the steps of compressing a fluid filled compressible object by movement of the joint(s), recording the change in pressure of the fluid within the object with respect to time, calculating the logarithm of the pressure, calculating the rate of change of the logarithm of the pressure with respect to time between two predetermined pressures during which the rate is substantially linear, and comparing that gradient with data relating to the rate of change achieved by movement of a normal joint.

BRIEF DESCRIPTION OF THE DRAWINGS

One embodiment of the present invention will now be described with reference to the accompanying drawings in which.

DESCRIPTION OF THE PREFERRED EMBODIMENTS

Figures 1, 2:
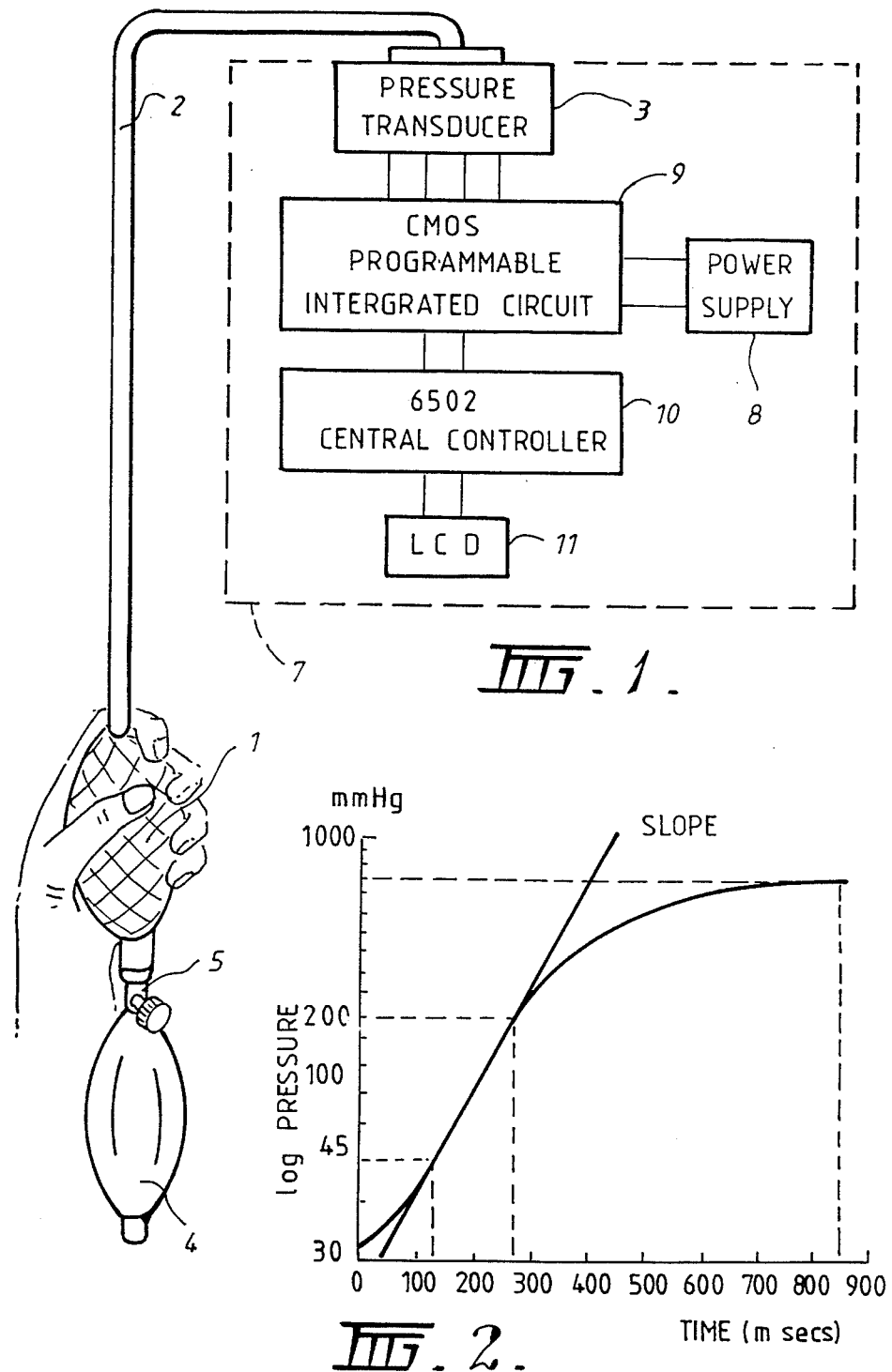
FIG. 1 is a schematic representation of an apparatus embodying the invention.
FIG. 2 is a schematic representation showing the relationship between the pressure produced by the apparatus of FIG. 1 as a function of time.

The apparatus shown in FIG. 1 of the drawings is one preferred embodiment for the assessment of hand function although it will be appreciated that the principles of that apparatus are equally applicable to the assessment of the functionality of other joints. The apparatus shown consists of an inflatable bladder 1 connected by means of a flexible tube 2 to a pressure transducer 3, such as a Type LX 1602G, manufactured by National Semiconductors.

The bladder 1 is inflatable by means of a squeeze pump 4 and valve 5, such as are normally used on a sphygmomanometer used by doctors in the measurement of blood pressure. In the present embodiment, the bladder 1 is generally pear-shaped and comprises a sygmoidoscope double-bellows in which the one-way valve is replaced by a pressure release valve. A bladder of this shape has been found to provide more consistent readings than other bladder shapes and allowed the small muscles of the hand and the long muscles of grip, as well as the full function of all joints involved to be assessed. When inflated to about 25 mm Hg, the bladder is about 10 cm long, 7 cm in breath and 4 cm in depth is palm-sized and is almost spherical in cross-section. The bladder 1 is then preferably retained within a mesh or net 6 so that when inflated it retains the shape imposed upon it by the net 6 and does not balloon outwardly at its ends when compressed. The bladder 1 is gripped by the patient in the manner shown in FIG. 1.

The pressure transducer 3 is mounted in a casing 7 which also contains the circuitry for analysing the changes in pressure in the fluid in the bladder 1 as it is gripped by the patient. That circuitry is shown schematically in FIG. 1 of the drawings and will be seen to comprise a power supply 8, comprising a rechargeable battery and a mains operated supply of standard configuration, a programmable integrated circuit, such as a CMOS programmable array, connected to the output from the pressure transducer 3, and which includes a timer, a central controller 10, such as Type 6502 integrated circuit, which drives three liquid crystal display (LCD) 11 capable of alternately displaying two screens by actuation of a toggle switch (not shown). If necessary, a reset button (not shown) is provided to reset the circuitry before each reading is taken. Similarly, a toggle switch (not shown), is provided to enable the operator to select different pressure ranges as will be explained below.

The programmable integrated circuit 9 may be replaced by a special purpose integrated circuit, and in either case the circuit is programmed or structured to analyze the pressure and time signals to provide (1) a maximum pressure output, (2) outputs of the elapsed time for the pressure to reach predetermined levels, (3) calculation of the logarithm of the pressure signal by any suitable mathemathical method, (4) calculation of the time rate of change of the logarithm of the pressure signal between predetermined lower and upper pressure levels, and (5) calculation of the correlation coefficient of the linear portion of the log pressure v time function between said predetermined pressure levels. In the present embodiment, the programmable integrated circuit 9 is programmed to record the elapsed times for the pressure signal to reach 60, 120 and 180 mm Hg or to reach 45, 60, 120 mm Hg. The alternative elapsed times are outputed by the circuit 9 in accordance with the position of the toggle switch referred to above which is selected by the operator according to the patient being assessed. Where the patient is known to have an affected hand, such as by Rheumatoid Arthritis, the lower pressure levels are selected since the higher levels will not be achievable by such patients.

In operation, the bladder 1 is inflated by the squeeze pump 4 and valve 5 to an initial pressure which is typically about 25 mm Hg. The bladder is then grasped by the patient and squeezed as firmly and as rapidly as possible resulting in an exponential change in pressure of the fluid within the bladder 1. FIG. 2 illustrates schematically a typical result for a normal person, the pressure being represented on the ordinate logarithmically. A logarithmic scale was chosen for the pressure ordinate since research data showed that the change in pressure was substantially logarithmic in nature.

The schematic curve illustrated in FIG. 2 of the drawings will be seen to include a small initial non-linear portion due to the inertia of the bladder and like effects, a substantially linear region between about 45 and 200 mm Hg, and a plateau or maximum pressure which is reached after about 500 to 600 milliseconds.

The display 11 indicates on its first screen the maximum grip strength in mm Hg or maximum pressure achieved, which is typically in the vicinity of 800 mm Hg, as well as the elapsed time for the pressure to reach the three predetermined pressures referred to above. When the toggle switch is actuated, the second screen of display 11 indicates the magnitude of the grip rate, that is, the slope of the straight line shown in FIG. 2 of the drawings, in log mm Hg/mS, the correlation coefficient of the straight line and the maximum grip strength is again displayed. The displays are preferably alphanumeric, and the values displayed may be identified in an abbreviated manner such as grip rate=Gr Rate, Correlation Coefficient=C Coeff and maximum grip strength=MGS As mentioned above, the correlation coefficient is used to inform the operator whether the bladder 1 has been gripped properly by the patient. Lack of correlation or lack of linearity in the linear portion of the log pressure v time function indicates an ineffective grip-action on the part of the patient. This is irrespective of the nature of the patient, it being understood that the lower pressure levels for the linear portion are selected in the case of a diseased hand. Where the correlation coefficient is of the order of 0.7 or 0.8, the operator will be aware that the grip action has not been effective.

It will be apparent from FIG. 2 that the pressure curve for normal subjects is substantially linear between approximately 45 and 200 mm Hg pressure and thus the slope of the straight line between these pressures conveniently represents grip rate, which is the time rate of change of the logarithmic pressure. However, as mentioned above these upper and lower pressure limits are different for diseased subjects.

It has been experimentally determined that the grip rate of individual patients is remarkably independent of age, strength and sex being approximately 0.04 log mm Hg/mS and in normal cases the grip rate achievable by the left hand is substantially identical to that achievable by the right hand.

This is a very important experimental finding since it enables the damage done to, say, a damaged left hand, to be assessed by measuring the grip rate of the damaged left hand and comparing it with the grip rate of the individual's undamaged right hand which is thus presumed to be the grip rate of the originally undamaged left hand. In this way, the percentage of the damage done to a partially damaged left hand can be assessed This is of particular importance where the damage is permanent and financial assessment of the damage is required for legal or insurance purposes. It is thought that an analogous result will apply to other body joints such as the knee and elbow. However, for use in relation to these joints the apparatus requires modification by the use of springs and strain gauges rather than the above described bladder and pressure transducers.

A number of physiological experiments have been conducted to determine the sensitivity of the apparatus of the invention in measuring controlled altered states interfering with grip. The behaviour of grip rate and grip strength as measured by the apparatus under conditions of (a) venous congestion, (b) ischaemia, and (c) splinting has been investigated. In each of these experiments, the right hand was used as a control while the left hand was restricted or modified. In each case, a significant deterioration in both the grip rate and the grip strength of the left hand as measured by the apparatus of the present embodiment was detected. The experiments therefore show that the apparatus may be used to objectively and quantitatively assess the function of the hand and other joints.

It will be apparent to those skilled in the art that the apparatus of the present invention will be used by Rheumatologists, Neurologists, Occupational Therapists, Physiotherapists, Medico-Legal Practitioners, and other Medical Officers.

The apparatus has obvious application in the assessment monitoring of diseases such as the treatment of hand injuries—be it injuries to nerve, tendon or muscle involved in hand function. Also it can be used in monitoring the extent of function loss incurred from these injuries or from Poliomyelitis, rheumatoid arthritis or more recently Repetitive Strain Injuries. neck Injuries involving the brachial plexus can be assessed, as well as chronic diseases such as rheumatoid arthritis, Parkinson's disease or even syringomyelia. Myxoedema effect and its response to therapy can also be monitored with this instrument.

The apparatus has obvious application in the monitoring of treatment of hand injuries, tendon, nerve and muscle injuries whether of traumatic origin, or viral origin as in the case of polio. Neck injuries such as brachial plexus damage are also able to be monitored with the apparatus. Other applicable diseases include non-rheumatoid arthritis, carpal tunnel disease, cerebral ischaemic diseases including Parkinson's disease, metabolic diseases as in myxoedema or myasthenia gravis, and neoplastic diseases as in brain tumours, or congenital diseases of the central nervous system such as Syringomyelia.

The foregoing describes only one embodiment of the present invention and modifications, obvious to those skilled in the art, can be made thereto without departing from the scope of the present invention. For example, the pressure transducer 3 can be replaced by a strain gauge system where it is intended to measure the grip rate of different joints. Similarly, the display 11 may be replaced by any desired number of digital or analogue meters or by a chart recording device. Preferably, provision is made from a chart recorder to be attached to the apparatus described above so that a permanent record of the results of a test may be kept. Other muscle resistance devices can also be substituted for the bladder 1.

I claim:

1. An apparatus for measuring the rate at which movement of a joint compresses a compressible object, comprising a fluid filled compressible object, such as an inflatable bladder, a pressure transducer in fluid connection with said object, circuit means connected to the pressure transducer and output display means connected to circuit means, said circuit means including means for determing the rate of change with time of the logarithm of the pressure of the fluid in said object between predetermined lower and upper pressure levels between which said rate of change is substantially linear, said output display means connected to said circuit means to display said rate of change.

2. An apparatus for assessing the functionality of a joint in which movement of a joint compresses a compressible object, comprising a fluid filled compressible object, such as an inflatable bladder, a pressure transducer in fluid communication with said object and circuit means connected to said pressure transducer, and display or recording means connected to said circuit means, said circuit means including for
   (1) calculating the logarithm of the pressure signal produced by said transducer,
   (2) timing the changes in said pressure signal,
   (3) determining the time rate of change of said logarithm of said pressure signal between predetermined lower and upper pressures during which said rate of change is substantially linear,
   (4) calculating the correlation coefficient of the linear portion of said rate of change whereby the effectiveness of the compression of the compressible object may be assessed, and
   (5) driving said display or recording means which displays or records said rate of change as a numerical value.

3. The apparatus of claim 2, wherein said circuit means further includes means for determining the elapsed a time for said pressure to reach said predetermined lower and upper pressures and to reach a third predetermined intermediate pressure.

4. The apparatus of claim 1, further comprising displaying or recording means for displaying or recording said elapsed times and said correlation coefficient.

5. The apparatus of claim 3 for the testing of hand functions, wherein said predetermined lower and upper pressures are 50 and 180 mm Hg respectively and said intermediate pressure is 120 mm Hg for relatively normal hand functions and wherein said predetermined pressures are 45, 120 and 60 mm Hg respectively for relatively affected hand functions.

6. The apparatus of claim 4 further comprising means connected to the circuit means to display or record a maximum pressure reached during each test.

7. A method of assessing the functionality of a joint or joints, comprising the steps of compressing a fluid containing bladder by movement of the joint(s), recording the change in pressure of the fluid within the bladder with respect to time, calculating the logarithm of said recorded pressures, calculating the rate of change of the logarithm of the recorded pressures with respect to time between two predetermined pressures during which said rate of change of the logarithm is substantially linear, calculating the correlation coefficient of said linear portion of said rate of change, and comparing that rate of change and correlation coefficient with data relating to the rate of change achieved by movement of a substantially normal joint.

8. The method of claim 7, further comprising the step of recording the elapsed time at which said predetermined lower and upper pressures are achieved and the elapsed time at which time a third predetermined intermediate pressure is achieved.

* * * * *